US012577252B2

(12) United States Patent
Tets et al.

(10) Patent No.: US 12,577,252 B2
(45) Date of Patent: Mar. 17, 2026

(54) DRUG FOR THE TREATMENT OF DISEASES CAUSED BY BACTERIA

(71) Applicants: Georgy Viktorovich Tets, Saint Petersburg (RU); Viktor Veniaminovich Tets, Saint Petersburg (RU); Konstantin Andreevich Krasnov, Saint Petersburg (RU)

(72) Inventors: Georgy Viktorovich Tets, Saint Petersburg (RU); Viktor Veniaminovich Tets, Saint Petersburg (RU); Konstantin Andreevich Krasnov, Saint Petersburg (RU)

(73) Assignees: Georgy Viktorovich Tets, Saint Petersburg (RU); Victor Veniaminovich Tets, Saint Petersburg (RU)

( * ) Notice: Subject to any disclaimer, the term of this patent is extended or adjusted under 35 U.S.C. 154(b) by 677 days.

(21) Appl. No.: 17/919,134

(22) PCT Filed: Apr. 14, 2021

(86) PCT No.: PCT/RU2021/050101
§ 371 (c)(1),
(2) Date: Oct. 14, 2022

(87) PCT Pub. No.: WO2021/211020
PCT Pub. Date: Oct. 21, 2021

(65) Prior Publication Data

US 2023/0212179 A1 Jul. 6, 2023

(30) Foreign Application Priority Data

Apr. 14, 2020 (RU) ........................... RU2020113508

(51) Int. Cl.
*C07D 491/052* (2006.01)
*A61P 31/04* (2006.01)

(52) U.S. Cl.
CPC .......... *C07D 491/052* (2013.01); *A61P 31/04* (2018.01)

(58) Field of Classification Search
CPC ................ A61K 2300/00; A61K 31/43; A61K 31/505; A61K 31/519; A61K 31/5383; A61K 31/635; A61K 31/65; A61K 45/06; A61P 31/04; C07D 491/052; Y02A 50/30
See application file for complete search history.

(56) References Cited

U.S. PATENT DOCUMENTS

2008/0004262 A1 1/2008 Ohrai et al.

FOREIGN PATENT DOCUMENTS

RU 2380370 C2 1/2010

OTHER PUBLICATIONS

Santacroce et. al. ("Advances and Challenges in Sepsis Management: Modern Tools and Future Directions", Cells, 13(5), 429) (Year: 2024).*
International Search Report dated Sep. 9, 2021 issued in corresponding application PCT/RU2021/050101 (2 pages).
Khan Khalid Mohammed et al: "Antibacterial activities of some arylidene barbiturate derivatives", Journal of the Chemical Society of Pakistan, 2013, 35(3), pp. 890-893.
Naya S. et al: "Novel photo-induced oxidative cyclization of 1,3-dimethyl-5-(1-arylmethylidene)pyrimidine-2,4,6(1,3,5H)-triones: synthesis and properties of areno[5,6]pyrano[2,3-d]pyrimidine-2,4(1,3H)-dionylium ions and their photo-induced autorecycling oxidizing reaction toward some amines", Tetrahedron, Apr. 12, 2005, 61(21), pp. 4919-4930.
Figueroa-Villar J.D. et al: "Nuclear magnetic resonance and molecular modeling study of exocylic carbon-carbon double bond polarization in benzylidene barbiturates", Journal of Molecular Structure, 2013, 1034, pp. 310-317.
Written Opinion of the International Searching Authority dated Sep. 9, 2021 issued in corresponding application PCT/RU2021/050101 (4 pages).
Spízek J. et al: "Lincomycin, clindamycin and their applications", Appl Microbiol Biotechnol, Feb. 5, 2004, vol. 64, Iss. 4, pp. 455-464.
Lincocin (lincomycin) dosing, indications, interactions, adverse effects, and more, Medscape, pp. 1-9. URL: https://reference.medscape.com/drug/lincocin-lincomycin-342555#0.

* cited by examiner

*Primary Examiner* — Jeffrey H Murray
*Assistant Examiner* — Daniel John Burkett
(74) *Attorney, Agent, or Firm* — Millen, White, Zelano & Branigan, P.C.; Jennifer L. King

(57) ABSTRACT

The invention relates to chemistry and pharmacology, specifically to a synthetic biologically active substance—7,9-dibromo-2,4-dioxo-1,2,3,4-tetrahydrochromeno[2,3-d]-pyrimidinium-10 acetate or succinate formula 1:1

1

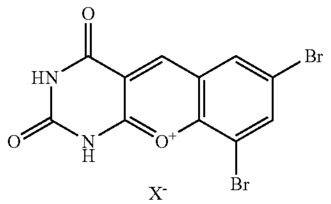

Where $X^-$=$CH_3COO^-$ or $HOOCCH_2CH_2COO^-$,
as well as its tautomeric, hydrated forms, solvate, complex compounds, adducts and salt forms, possessing antimicrobial activity, and the ability to penetrate bacterial biofilms. The compound is intended for the treatment of bacterial infections of the oropharynx, skin, and mucous membranes, urinary system, implants, respiratory system, gastrointestinal tract. osteomyelitis, sepsis, nosocomial and wound infections.

13 Claims, No Drawings

DRUG FOR THE TREATMENT OF DISEASES CAUSED BY BACTERIA

TECHNICAL FIELD

The invention relates to chemistry and pharmacology, specifically to a synthetic biologically active substance—7, 9-dibromo-2,4-dioxo-1,2,3,4-tetrahydrochromeno[2,3-d]-pyrimidinium-10 acetate, having antimicrobial activity, and the method of its synthesis.

The invention extends to all spatial isomers of the claimed substance, all its tautomeric and salt forms, as well as hydrated forms, solvates, complex compounds and adducts with organic substances.

The substance is intended for use in medical practice for the treatment of diseases caused by bacteria, as well as for similar purposes in veterinary medicine. The substance can be used both individually and in the form of their pharmacologically acceptable salts, complexes, as well as in combination with other drugs and complexes.

BACKGROUND ART

The range of diseases associated with bacteria is rapidly expanding, among which the most relevant are *Staphylococcus* spp, *Streptococcus* spp, *Listeria* spp, *Rothia* spp, various representatives of sporobiota and others (Clinical Pharmacist, September 2017, Vol 9, No 9, online|DOI: 10.1211/CP.2017.20203363 Tetz, G., & Tetz, V. (2017) Introducing the sporobiota and sporobiome Gut Pathogens, 9:38 DOI 10.1186/s13099-017-0187-8).

The high variability of bacteria, leading to the emergence and rapid spread of resistance to antibiotics, does not allow achieving a sufficient clinical effect in the treatment of a large number of diseases caused by them of various localization. A particular problem is the spread of multiple drug resistance. This problem is especially relevant for the treatment of infections caused by MRSA and VRSA strains of *Staphylococcus* spp and *Streptococcus* spp (J Glob Infect Dis. 2010 September-December; 2(3): 275-283. Methicillin and Vancomycin Resistant *S. aureus* in Hospitalized Patients Poonam Sood Loomba, Juhi Taneja, and Bibhabati Mishra Emerging Infectious Diseases•www.cdc.gov/eid•Vol. 11, No. 10, 2005 1539-1544 Jon P. Furuno*, Eli N. Perencevich*†‡, Judith A. Johnson*†, Marc-Oliver Wright‡2, Jessina C. McGregor*, J. Glenn Morris*†, Sandra M. Strauss*, Mary-Claire Roghman*†, Lucia L. Nemoy*†, Harold C. Standiford‡, Joan N. Hebden‡, and Anthony D. Harris Methicillin-resistant *Staphylococcus aureus* and Vancomycin-resistant Enterococci Co-colonization DOI: 10.3201/eid1110.050508

J Hosp Infect. 2018 February; 98(2):111-117. doi: 10.1016/j.jhin.2017.11.008. Epub 2017 Nov. 22. *Staphylococcus aureus* and *Staphylococcus epidermidis* infections on implants. Oliveira WF1, Silva PMS1, Silva RCS2, Silva GMM2, Machado G2, Coelho LCBB1, Correia MTS3. The present invention is devoted to the solution of the problem of combating bacteria with multiple resistance to existing antimicrobial drugs.

The prototype of the invention, the closest in terms of the spectrum of antimicrobial activity, was the antibiotic lincomycin, which inhibits protein synthesis in a microbial cell (https://reference.medscape.com/drug/lincocin-lincomycin-342555) Lincomycin is a product of *Streptomyces lincolnensis* with the following structure:

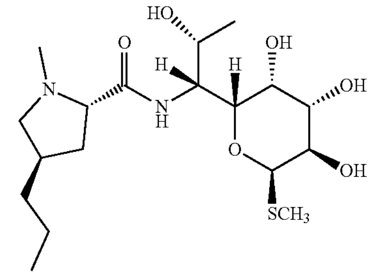 [SMILES: CCC[C@@H]1C[C@@H](C(=O)N[C@@H]([C@H]2O[C@H](SC)[C@H](O)[C@@H](O)[C@H]2O)[C@@H](C)O)N(C)C1]

Lincomycin is a narrow-spectrum antibiotic that is active primarily against firmicute bacteria. At the same time, it has no effect on methicillin- and vancomycin-resistant strains of *Staphylococcus aureus* and *Streptococcus* spp, (MRSA and VRSA) (Appl. Microbiol. Biotechnol. 2004 May; 64(4): 455-64. Epub 2004 Feb. 5. Lincomycin, clindamycin and their applications Spízek J1, Rezanka T.).

SUMMARY OF THE INVENTION

The objective of the invention is to create a new chemical compound with high antibacterial activity and high efficiency in the treatment of diseases caused by bacteria, including bacteria with multiple resistance to existing antimicrobial drugs.

According to the invention, the problem is solved by synthesizing a new antimicrobial substance of the formula (1):

1

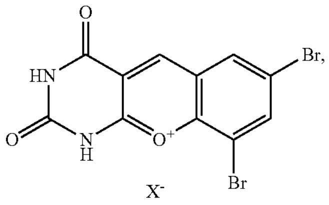

Where $X^-$=$CH_3COO^-$ or $HOOCCH_2CH_2COO^-$.

Examples of the invention include all spatial isomers of the claimed substance, all its tautomeric and salt forms, complex compounds, as well as hydrated forms and adducts with organic substances.

Also proposed is a pharmaceutical composition for the treatment of diseases caused by bacteria, containing an effective amount of a compound of formula 1 or its tautomeric, hydrated form, salt, solvate, complex compound and adduct, and a pharmaceutically acceptable carrier or adjuvant.

Also proposed is the use of a compound of formula 1 for the treatment of diseases caused by bacteria, including, but not limited to, bacterial infections of the oropharynx, skin, mucous membranes, urinary system, implants, respiratory system, gastrointestinal tract, osteomyelitis, sepsis, nosocomial and wound infections, as well as to suppress the viability of bacteria that are part of biofilms.

According to another aspect of the invention, the pharmaceutical composition contains an effective amount of a compound of formula 1 in combination with at least one other antimicrobial drug.

According to the invention the compound of formula 1 is used in compositions with at least one other antimicrobial drug for the treatment of diseases caused by antibiotic-resistant strains of MRSA, VISA, VRSA.

According to another aspect of the invention, a method of treating diseases caused by bacterial infections is provided, comprising administering to a subject in need of such treatment an effective amount of a compound of formula 1 or its tautomeric, hydrated form, salt, solvate, complex compound and adduct, or a pharmaceutical composition containing it.

In a further aspect of the invention, the disease is a disease caused by staphylococci or streptococci.

In yet another further aspect of the invention, said disease is a disease caused by *Staphylococcus aureus.*

In another additional aspect of the invention, said disease is selected from the group including bacterial infections of the oropharynx, skin, mucous membranes, urinary system, implants, respiratory system, gastrointestinal tract, osteomyelitis, sepsis, nosocomial and wound infections.

In another aspect of the invention, the compound of formula 1 or its tautomeric, hydrated form, salt, solvate, complex compound and adduct is administered at a dosage of 0.5 mg/kg to 2000 mg/kg.

In yet another aspect of the invention, the compound of formula 1 or its tautomeric, hydrated form, salt, solvate, complex compound and adduct is administered at a dosage of from 1 mg/kg to 1500 mg/kg, more preferably from 5 mg/kg to 1000 mg/kg, even more preferably 10 mg/kg to 500 mg/kg, even more preferably 10 mg/kg to 400 mg/kg, even more preferably 10 mg/kg to 350 mg/kg, even more preferably 10 mg/kg up to 300 mg/kg, even more preferably 10 mg/kg to 250 mg/kg, even more preferably 10 mg/kg to 200 mg/kg, even more preferably 10 mg/kg to 150 mg/kg, even more preferably 10 mg/kg to 100 mg/kg.

In another aspect of the invention, the compound of formula 1 or its tautomeric, hydrated form, salt, solvate, complex compound and adduct is administered at a dosage of 0.5 mg/kg to 2 mg/kg, 1 mg/kg to 10 mg/kg, 5 mg/kg to 30 mg/kg, preferably 10 mg/kg to 100 mg/kg, even more preferably 50 mg/kg to 150 mg/kg.

In a further aspect of the invention, said compound of formula 1 or its tautomeric, hydrated form, salt, solvate, complex compound and adduct, or a pharmaceutical composition containing it, is administered enterally to a subject.

The applicant is not aware of any sources of information that would contain information about identical technical solutions, which allows us to conclude that the claimed invention complies with the "Novelty" (N) criterion.

The applicant has not identified any sources of information containing information about the impact of the claimed distinctive features on the technical result achieved as a result of their implementation. This, according to the applicant, indicates the compliance of this technical solution with the criterion of "Inventive step" (IS).

In the following, the invention is explained by a detailed description of examples of its implementation without reference to the drawings.

PREFERRED EMBODIMENT

Best Mode for Carrying Out the Invention

The claimed substance is synthesized in accordance with scheme 1.

Scheme 1

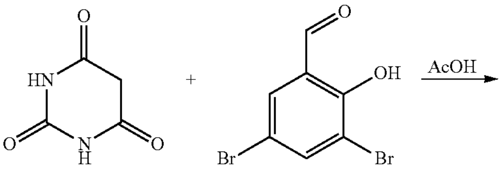

2 3

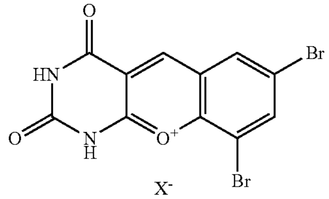

1

Where $X^-$=$CH_3COO^-$ or $HOOCCH_2CH_2COO^-$

The synthesis of the claimed substance 1 according to scheme 1 is carried out in one stage.

The essence of the invention is illustrated by the following examples of the synthesis of the claimed substance and its characteristics, experiments to study the biological properties and tables of the results of experiments to determine the biological properties of the claimed substance, where:

- example 1—a specific variant of the synthesis of the claimed substance (Compound 1a);
- example 2—a specific variant of the synthesis of the claimed substance (Compound 1a);
- example 3—a specific variant of the synthesis of the claimed substance (Compound 1b);
- example 4—determination of the effectiveness of the test compounds on firmicutes bacteria;
- example 5—determination of the effectiveness of the test compounds on gracilicutes and wall-less bacteria;
- example 6—the effect of the claimed compounds on bacterial strains with multiple resistance to antibiotics;
- example 7—the effect of the claimed compound on bacteria that are part of biofilms;
- example 8—study of chemotherapeutic efficacy.
- example 9—clinical data on the effectiveness of the claimed compound in the treatment of tonsillitis caused by *staphylococcus* or *streptococcus;*
- example 10—use of the compound in the form of a composition with other antimicrobials.

Example 1. A Variant of the Synthesis of the Claimed Substance is the Preparation of 7,9-dibromo-2,4-dioxo-1,2,3,4-tetrahydrochromeno[2,3-d]-pyrimidinium-10 acetate (Compound 1a)

0.1 mol (12.8 g) of barbituric acid (2) was dissolved with heating in 270 ml of glacial acetic acid. 0.105 mol (29.4 g) of 3,5-dibromo-2-hydroxybenzaldehyde (3) was added to this solution with stirring, and the resulting reaction mixture was left at room temperature for 40 h. The resulting crystalline product was filtered off, washed with cold acetic acid, then with ether, and dried on air. 30.7 g of product 1 (Compound 1a) was obtained in the form of yellow needle-like crystals with mp 255-260° C. (decomp.). Yield 71% of theory.

Elemental analysis data. Found, %: C, 36.31; H, 2.01; Br, 36.87; N, 6.44. C13H8Br2N2O5. Calculated, %: C, 36.14; H, 1.97; Br, 36.99; N, 6.48.

NMR spectrum in DMSO-d6. Chemical shift, ppm (J, Hz): 7.75 d (1H, J 8.2, ArH), 7.92 d (1H, J 8.2, ArH), 8.29 s (1H, =CH), 11.18 s (1H, NH), 11.44 (1H, NH).

mass spectrum. MH+ (I, %) 391 (24), 373 (100).

Example 2. A Variant of the Synthesis of the Claimed Substance is the Preparation of 7,9-dibromo-2,4-dioxo-1,2,3,4-tetrahydrochromeno[2,3-d]-pyrimidinium-10 acetate (Compound 1a)

0.1 mol (12.8 g) of barbituric acid (2) was dissolved with heating in 300 ml of glacial acetic acid. To this solution was added with stirring 0.11 mol (30.8 g) of 3,5-dibromo-2-hydroxybenzaldehyde (3) and then 0.2 mol (20.4 g) of acetic anhydride. The resulting reaction mixture was left at room temperature for 24 h. The resulting crystalline product was filtered off, washed with cold acetic acid, then with ether, and dried in air. 36.6 g of product 1 were obtained in the form of yellow needle-shaped crystals with mp 255-260° C. (with decomposition). Yield 80% of theoretical. The characteristics of the product (Compound 1a) are the same as in Example 1.

Example 3. A Variant of the Synthesis of the Claimed Substance is the Preparation of 7,9-dibromo-2,4-dioxo-1,2,3,4-tetrahydrochromeno[2,3-d]-pyrimidinium-10 succinate (Compound 1b)

0.1 mol (12.8 g) of barbituric acid (2) was dissolved with heating in 300 ml of glacial acetic acid. To this solution was added with stirring 0.105 mol (29.4 g) of 3,5-dibromo-2-hydroxybenzaldehyde (3) and then 0.2 mol (20.4 g) of succinic anhydride. The resulting reaction mixture was left at room temperature for 24 h. The resulting crystalline product was filtered off, washed with ether, and dried in air. 37.8 g of product 1b were obtained in the form of yellow needle-shaped crystals with mp 250-253° C. (with decomposition). Yield 73% of theoretical.

Elemental analysis data Compounds 1b. Found, %: C, 36.39; H, 2.09; Br, 32.54; N, 5.66. C15H10Br2N2O7. Calculated, %: C, 36.76; H, 2.06; Br, 32.61; N, 5.72.

Example 4 Determination of the Effectiveness of the Test Compounds Against Firmicutes Bacteria Determination of the antimicrobial activity of substances was carried out on dense and liquid nutrient media. To assess the minimum inhibitory concentration (MIC), the serial dilution method was used, according to the recommendations of CLSI (Clinical Laboratories and Standards Institute, formerly National Committee for Clinical Laboratory Standards) (Clinical Laboratories and Standards Institute. Methods for Dilution Antimicrobial Susceptibility Tests for Bacteria That Grow Aerobically; Approved Standard—Seventh Edition Document M7-A7 CLSI, Wayne, Pa., 2006; Clinical Laboratories and Standards Institute).

The assessment of the antimicrobial activity of substances against firmicute bacteria was performed on fresh clinical isolates of strains of *Streptococcus pyogenes, Streptococcus mitis, Bacillus subtilis, Bacillus cereus, Corynebacterium ulcerans, Micrococcus luteus.*

TABLE 1

Determination of the effectiveness of the test compounds (Compounds 1a and 1b) on firmicutes bacteria

| Compounds prepared according to the invention | MIC (μg/ml) | | | | | | | |
|---|---|---|---|---|---|---|---|---|
| | *S. aureus* ATCC 29213 | *S pyogenes* | *S. mitis* | *B. subtilis* | *B. cereus* | *L. monocytogenes* | *C. ulcerans* | *M. lutteus* |
| 1a | 0.5 | 0.1 | 0.1 | 1.0 | 1.0 | 1.0 | 0.5 | 1.0 |
| 1b | 1.0 | 2.0 | 2.0 | 2.0 | 4.0 | 4.0 | 2.0 | 2.0 |

As shown by the tests, Compound 1a and its salt have a high antimicrobial activity against firmicutes bacteria.

Example 5. Determination of the Effectiveness of the Test Compounds on Gracilicutes and Wall-Less Bacteria The study of the effect on strains was performed on fresh clinical isolates of *Haemophilus influenzae, Neisseria meningitides, Ureaplasma urealyticum* strains, as well as on the *Escherichia coli* ATCC29592 strain.

TABLE 2

Determination of the effectiveness of the action of the tested Compounds 1a and 1b on gracilicutes and wall-less bacteria

| Compound | MIC (μg/ml) | | | |
|---|---|---|---|---|
| | *E. coli* | *H. influenzae* | *N. meningitides* | *U. urealyticum* |
| 1a | 20.0 | 10.0 | 10.0 | 10.0 |
| 1b | 30.0 | 20.0 | 20.0 | 20.0 |

As can be seen from the table, the claimed Compounds 1a and 1b have antimicrobial activity against some gracilicutes and wall-less bacteria.

Example 6. The Effect of the Claimed Compounds on Bacterial Strains with Multiple Resistance to Antibiotics The study of the effect of Compound 1a on strains with multiple resistance to existing antibiotics was performed on fresh clinical isolates of strains: *S. aureus* VT-V-18, *S. aureus* VT-E-25 *S. aureus* VT-A-199 and *S. aureus* VT-P-82, as well as *S. aureus* strain American Type Culture Collection (Rockville, Md.) and strains *S. aureus* SA77 and *S. aureus* SA85,

TABLE 3

Effects of Compound 1a on various strains of *S. aureus*.

| | | MIC (μg/ml) | | | | | | |
|---|---|---|---|---|---|---|---|---|
| | | Strains MRSA | | | | Strains VRSA | | Strain MSSA |
| Compound | Resistance | VT-V-18 | VT-E-25 | VT-A-199 | VT-P-82 | SA77 | SA85 | ATCC 29213 |
| 1a | Not detected (ND) | 0.5 | 1.0 | 1.0 | 2.0 | 0.5 | 1.0 | 0.5 |

Substance 1a is highly active at concentrations from 0.5 to 2.0 mg/kg. The efficacy of Compound 1a did not differ between methicillin/vancomycin-resistant and susceptible strains.

Example 7. The Action of the Claimed Compound on Bacteria that are Part of Biofilms

*S. aureus* ANCC29213 bacteria were grown in a 24-well plateau in LB medium for 24 hours at 37° C. After that, Compound 1a and lincomycin (8 wells for each preparation and control without preparations) were added to the wells at final concentrations of 10 μg/ml and incubated for 24 hours at 37° C. After incubation, the medium was removed, the biofilms were washed with a sterile solution of isotonic sodium chloride, the biofilms were removed from the bottom of the wells, resuspended in isotonic sodium chloride solution, and the number of colony forming units (CFU) was determined by the method of serial dilutions.

TABLE 4

Survival of bacteria in biofilms

| Compound | Number of CFU |
|---|---|
| Control | $3.0 \pm 1.0 \times 10^8$ |
| Lincomycin | $2.0 \pm 1.0 \times 10^8$ |
| Compound 1a | $4.0 \pm 1.0 \times 10^5$ |

Substance 1a is highly active at concentrations from 0.5 to 2.0 mg/kg. The efficacy of Compound 1a did not differ between methicillin/vancomycin-resistant and susceptible strains.

Example 7. The Action of the Claimed Compound on Bacteria that are Part of Biofilms The data obtained show that Compound 1a penetrates into bacterial biofilms and reduces the number of bacteria capable of growth in them by 1000 times. The reference drug does not penetrate into bacterial biofilms and does not change the number of CFUs in them.

Example 8 Chemotherapeutic Efficacy Study

To study the chemotherapeutic efficacy, a model of acute generalized infection in small animals was used. C57BL6 mice were intraperitoneally infected with *Staphylococcus aureus* ATCC 38591 at a dose of 1×108 microbial cells. The infectious dose was established in preliminary studies. Mice infected with the same dose of microbial culture but not treated served as controls.

The preparations were dissolved in an isotonic sodium chloride solution and substance 1a or Lincomycin was administered. 2 hours after infection, the drugs were administered orally daily at doses of 10 to 100 mg/kg, 2 times a day.

The death of mice was taken into account daily for 7 days.

TABLE 5

Evaluation of the effect of Compound 1a in acute generalized infection in small animals infected with *Staphylococcus aureus* ATCC 38591*

| Dose | Number | Mice death (days) | | | | | | |
|---|---|---|---|---|---|---|---|---|
| (mg/kg) | of mice | 1 | 2 | 3 | 4 | 5 | 6 | 7 |
| | Infection with *Staphylococcus aureus* | | | | | | | |
| 100 | 10 | | | | | | | |
| 80 | 10 | | | | | | | |
| 50 | 10 | | | | | | | |
| 20 | 10 | | | 1 | | 1 | 2 | |
| 10 | 10 | | 1 | | | 1 | 2 | 1 |
| Control | 10 | 9 | 1 | | | | | |

*Averaged data from 3 independent experiments.

TABLE 6

Evaluation of the effect of Lincomycin in acute generalized infection in small animals infected with *Staphylococcus aureus* ATCC 38591*

| Dose | Number | Mices death (days) | | | | | | |
|---|---|---|---|---|---|---|---|---|
| (mg/kg) | of mice | 1 | 2 | 3 | 4 | 1 | 2 | 7 |
| | Infection with *Staphylococcus aureus* | | | | | | | |
| 100 | 10 | | | | | | | |
| 80 | 10 | | | | | | | |
| 50 | 10 | | | 1 | | 1 | 2 | |
| 20 | 10 | | | 1 | | 1 | 3 | |
| 10 | 10 | | 2 | | | 1 | 2 | 1 |
| Control | 10 | 8 | 2 | | | | | |

The results obtained indicate that the Compound according to the invention is highly effective in the treatment of diseases caused by *staphylococcus*, which in relation to human diseases means such diseases as inflammatory diseases of the oropharynx, including tonsillitis, purulent-inflammatory diseases of the skin and mucous membranes, cystitis, implant infections, osteomyelitis and sepsis, as well as pneumonia, and diseases of the gastrointestinal tract. The model used is also a reproduction of nosocomial infections resulting from diagnostic and surgical interventions.

Example 9. Clinical Data on the Effectiveness of the Claimed Compound in the Treatment of Tonsillitis Caused by *Staphylococcus* or *Streptococcus*

This pathology was chosen by us as one of the above lists to confirm the effectiveness and practical applicability of the claimed compound. The study was performed on two groups of patients, totaling 138 people, who received the drug enterally twice a day at doses from 500 mg to 2000 mg.

The compound was administered as a pharmaceutical composition containing Compound 1a in acetate form in an isotonic solution of a pharmaceutically acceptable sodium chloride carrier.

TABLE 7

The frequency of eradication of the pathogen in the bacteriological study of the material from the lacunae of the palatine tonsil in the treatment of tonsillitis.

| | Eradication | | | | |
|---|---|---|---|---|---|
| | Compound 1a | | Phenoxymethylpenicillin | | |
| Pathogen/ Day | Number of patients | % | Number of patients | % | |
| *S. aureus* | | | | | |
| 0 | | | | | |
| 4 | 63 | 85.14% | 3 | 4.11% | P < 0.001 |
| 8 | 68 | 91.89% | 7 | 9.59% | P < 0.001 |
| 14 | 70 | 94.59% | 10 | 13.70% | P < 0.001 |
| *S. pyogenes* | | | | | |
| 4 | 67 | 94.37% | 7 | 10.14% | P < 0.001 |
| 8 | 68 | 95.77% | 8 | 11.59% | P < 0.001 |
| 14 | 68 | 95.77% | 9 | 13.04% | P < 0.001 |

Thus, the effect of the claimed compound on the eradication of the pathogen is statistically significantly higher than at Phenoxymethylpenicillin, and the effect develops already on the 4th day of treatment.

The results obtained indicate that in the group of patients with tonsillitis, which is selected from the list of diseases of the possible use of the claimed compound, a high clinical efficacy of the claimed agent was registered, significantly exceeding that of the reference drug.

Example 10 Use of the Compound as a Composition with Other Antimicrobials

The claimed compound can be used in the form of a composition with other antimicrobial drugs, and in this case it is possible to achieve a total antibacterial effect that is superior to that which can be obtained with the independent use of these drugs.

We used a strain of *H. influenzae* grown on a liquid nutrient medium. The minimum inhibitory concentration was determined by the method of serial dilutions.

TABLE 8

The minimum inhibitory concentration (MIC) of 1a and its combinations with various antimicrobials in relation to *H. influenzae*.

| Compound | MIC (μg /ml) |
|---|---|
| Compound 1a | 10.0 |
| Tetracycline | 2.0 |
| Levofloxacin | 0.05 |
| Co-trimoxazole | 1.0 |
| Amoxicillin/clavulanate | 2.0 |
| 1a + Tetracycline | 3.0 + 0.53 |
| 1a + Levofloxacin | 3.0 + 0.01 |
| 1a + Co-trimoxazole | 3.0 + 0.5 |
| 1a + Amoxicillin/clavulanate | 3.0 + 0.05 |

The data obtained indicate that combinations of Compound 1a and an antibiotic taken in an amount less than its individual MIC (subinhibitory concentration) provide inhibition of growth of the test microbe.

INDUSTRIAL APPLICABILITY

Known materials and equipment are used to implement the invention, which, according to the applicant, determines the compliance of the invention with the criterion "Industrial applicability" (IA).

The invention claimed is:

1. A 7,9-dibromo-2,4-dioxo-1,2,3,4-tetrahydrochromeno[2,3-d]-pyrimidinium-10 compound of formula 1:

1

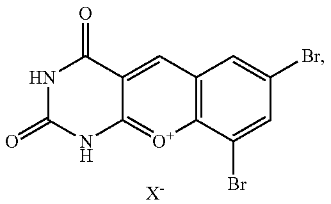

where $X^-$ is selected from the group consisting of $=CH_3COO^-$ and $HOOCCH_2CH_2COO^-$;

or tautomers, hydrated forms, solvates, or salt forms thereof.

2. A pharmaceutical composition comprising: (i) the 7,9-dibromo-2,4-dioxo-1,2,3,4-tetrahydrochromeno[2,3-d]-pyrimidinium-10 compound according to claim 1 or tautomers, hydrated forms, solvates, or salt forms thereof and (ii) a pharmaceutically acceptable carrier or diluent.

3. A pharmaceutical composition according to claim 2, further comprising at least one of Tetracycline, Levofloxacin, Co-trimoxazole, and Amoxicillin/clavulanate.

4. A method for treating bacterial infections in a subject by administering a pharmaceutical composition comprising (i) a 7,9-dibromo-2,4-dioxo-1,2,3,4-tetrahydrochromeno[2,3-d]-pyrimidinium-10 compound of Formula 1:

1

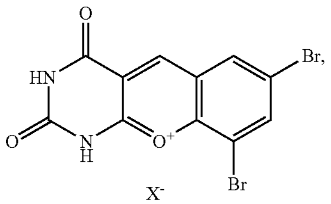

where $X^-$ is selected from the group consisting of $=CH_3COO^-$ and $HOOCCH_2CH_2COO^-$; or or tautomers, hydrated forms, solvates, or salt forms thereof; and (ii) a pharmaceutically acceptable carrier or diluent; wherein the bacterial infection is caused by at least one of firmicutes bacteria, *Staphylococcus aureus, Haemophilus influenzae, Neisseria meningitides, Ureaplasma urealyticum*, or *Escherichia coli.*

5. The method for treating bacterial infections of claim 4 wherein the compound of Formula 1 or a tautomer, hydrated form, solvate, or salt form thereof penetrates into bacterial biofilms.

6. The method for treating bacterial infections of claim 4, wherein the bacterial infection is selected from bacterial infections of the oropharynx, skin, mucous membranes, urinary system, implants, respiratory system, gastrointestinal tract, osteomyelitis, sepsis, nosocomial and wound infections.

7. The method for treating bacterial infections of claim 4, wherein, the compound is administered at a dosage of 0.5 mg/kg to 2000 mg/kg.

8. The method for treating bacterial infections of claim 4, wherein, said compound or pharmaceutical composition is administered to a subject enterally.

9. The method for treating bacterial infections of claim 4, wherein the bacterial infection is caused by at least one of Methicillin-resistant *Staphylococcus aureus* (MRSA), Vancomycin-resistant *Staphylococcus aureus* (VRSA), or Vancomycin-intermediate *Staphylococcus aureus* (VISA).

10. The method for treating bacterial infections of claim 4, wherein the bacterial infection is caused by at least one of Methicillin-resistant *Staphylococcus aureus* (MRSA) or Vancomycin-resistant *Staphylococcus aureus* (VRSA).

11. The method for treating bacterial infections of claim 4, wherein the pharmaceutical composition further comprises at least one of Tetracycline, Levofloxacin, Co-trimoxazole, and Amoxicillin/clavulanate.

12. The method for treating bacterial infections of claim 11, wherein the bacterial infection is caused by at least one of Methicillin-resistant *Staphylococcus aureus* (MRSA), Vancomycin-resistant *Staphylococcus aureus* (VRSA), or Vancomycin-intermediate *Staphylococcus aureus* (VISA).

13. The method for treating bacterial infections of claim 11, wherein the bacterial infection is caused by at least one of Methicillin-resistant *Staphylococcus aureus* (MRSA) or Vancomycin-resistant *Staphylococcus aureus* (VRSA).

* * * * *